US011306351B2

(12) United States Patent
Shapero

(10) Patent No.: US 11,306,351 B2
(45) Date of Patent: Apr. 19, 2022

(54) METHODS FOR GENOTYPING

(71) Applicant: AFFYMETRIX, INC., Carlsbad, CA (US)

(72) Inventor: Michael H. Shapero, Sunnyvale, CA (US)

(73) Assignee: AFFYMETRIX, INC., Carlsbad, CA (US)

( * ) Notice: Subject to any disclaimer, the term of this patent is extended or adjusted under 35 U.S.C. 154(b) by 203 days.

(21) Appl. No.: 16/155,771

(22) Filed: Oct. 9, 2018

(65) Prior Publication Data

US 2019/0071719 A1 Mar. 7, 2019

Related U.S. Application Data

(63) Continuation of application No. 15/184,469, filed on Jun. 16, 2016, now abandoned, which is a continuation of application No. 11/614,948, filed on Dec. 21, 2006, now Pat. No. 9,388,459.

(60) Provisional application No. 60/752,782, filed on Dec. 21, 2005.

(51) Int. Cl.
| *C12Q 1/6858* | (2018.01) |
| *C12Q 1/6809* | (2018.01) |
| *C12Q 1/6837* | (2018.01) |
| *C12Q 1/686*  | (2018.01) |
| *C12Q 1/6874* | (2018.01) |
| *C12Q 1/6876* | (2018.01) |
| *C12Q 1/6855* | (2018.01) |

(52) U.S. Cl.
CPC ........... *C12Q 1/6858* (2013.01); *C12Q 1/686* (2013.01); *C12Q 1/6809* (2013.01); *C12Q 1/6837* (2013.01); *C12Q 1/6855* (2013.01); *C12Q 1/6874* (2013.01); *C12Q 1/6876* (2013.01); *C12Q 2525/179* (2013.01); *C12Q 2535/125* (2013.01); *C12Q 2565/501* (2013.01); *C12Q 2565/514* (2013.01); *C12Q 2565/537* (2013.01); *C12Q 2600/156* (2013.01)

(58) Field of Classification Search
CPC .. C12Q 1/6858; C12Q 1/6809; C12Q 1/6837; C12Q 1/6876; C12Q 2600/156; C12Q 1/6853; C12Q 2525/161; C12Q 2525/155; C12Q 2525/191
See application file for complete search history.

(56) References Cited

U.S. PATENT DOCUMENTS

| 5,002,867 A | 3/1991 | Macevicz |
| 5,143,854 A | 9/1992 | Pirrung et al. |
| 5,202,231 A | 4/1993 | Drmanac et al. |
| 5,286,632 A | 2/1994 | Jones |
| 5,387,505 A | 2/1995 | Wu et al. |
| 5,427,932 A | 6/1995 | Weier et al. |
| 5,447,841 A | 9/1995 | Gray et al. |
| 5,472,842 A | 12/1995 | Stokke et al. |
| 5,492,806 A | 2/1996 | Drmanac et al. |
| 5,498,535 A | 3/1996 | Fomenkov et al. |
| 5,501,964 A | 3/1996 | Wigler et al. |
| 5,508,169 A | 4/1996 | Deugau et al. |
| 5,580,730 A | 12/1996 | Okamoto |
| 5,582,989 A | 12/1996 | Caskey et al. |
| 5,608,169 A | 3/1997 | Fujioka et al. |
| 5,624,825 A | 4/1997 | Walker et al. |
| 5,633,365 A | 5/1997 | Stokke et al. |
| 5,665,549 A | 9/1997 | Pinkel et al. |
| 5,667,972 A | 9/1997 | Drmanac et al. |
| 5,695,940 A | 12/1997 | Drmanac et al. |
| 5,700,637 A | 12/1997 | Southern |
| 5,700,642 A | 12/1997 | Monforte et al. |
| 5,700,673 A | 12/1997 | McElroy et al. |
| 5,710,000 A | 1/1998 | Sapolsky et al. |
| 5,710,028 A | 1/1998 | Eyal et al. |
| 5,721,098 A | 2/1998 | Pinkel et al. |
| 5,776,753 A | 7/1998 | Hillman et al. |
| 5,801,021 A | 9/1998 | Gray et al. |
| 5,830,645 A | 11/1998 | Pinkel et al. |
| 5,840,482 A | 11/1998 | Gray et al. |
| 5,854,033 A | 12/1998 | Lizardi et al. |

(Continued)

FOREIGN PATENT DOCUMENTS

| EP | 0534858 A1 | 3/1993 |
| EP | 1350853 A1 | 10/2003 |

(Continued)

OTHER PUBLICATIONS

Bortolin et al. Analytical Validation of the Tag-It High-Throughput Microsphere-Based Universal Array Genotyping Platform: Application to the Multiplex Detection of a Panel of Thrombophilia-Associated Single-Nucleotide Polymorphisms. Clinical Chemistry 2004; 50: 2028-2036. (Year: 2004).*

(Continued)

*Primary Examiner* — Angela M. Bertagna

(74) *Attorney, Agent, or Firm* — Workman Nydegger

(57) ABSTRACT

The present invention provides for methods for discriminating between alleles at polymorphic positions in a genome. In general, the methods employ allele-specific extension of oligonucleotides that are complementary to one of the alleles at the 3' end of the oligonucleotide. The allele-specific oligonucleotides are resistant to proofreading activity from a polymerase and may be extended in an allele-specific manner by a DNA polymerase with a functional 3' to 5' exonuclease activity. The allele-specific oligonucleotides may be attached to a solid support such as a chip or a bead.

18 Claims, 6 Drawing Sheets

(56) References Cited

U.S. PATENT DOCUMENTS

| | | | |
|---|---|---|---|
| 5,856,097 A | 1/1999 | Pinkel et al. |
| 5,858,656 A | 1/1999 | Deugau et al. |
| 5,858,671 A | 1/1999 | Jones |
| 5,965,362 A | 10/1999 | Pinkel et al. |
| 5,972,608 A | 10/1999 | Peterson et al. |
| 5,972,693 A | 10/1999 | Rothberg et al. |
| 5,976,790 A | 11/1999 | Pinkel et al. |
| 5,994,068 A | 11/1999 | Guilfoyle et al. |
| 6,045,994 A | 4/2000 | Zabeau et al. |
| 6,057,096 A | 5/2000 | Rothschild et al. |
| 6,100,030 A | 8/2000 | McCasky et al. |
| 6,103,463 A | 8/2000 | Chetverin et al. |
| 6,159,685 A | 12/2000 | Pinkel et al. |
| 6,180,349 B1 | 1/2001 | Ginzinger et al. |
| 6,197,510 B1 | 3/2001 | Vinayagamoorthy |
| 6,232,066 B1 | 5/2001 | Felder et al. |
| 6,232,068 B1 | 5/2001 | Linsley et al. |
| 6,248,877 B1 | 6/2001 | Bonner et al. |
| 6,258,539 B1 | 7/2001 | Hunkapiller et al. |
| 6,261,770 B1 | 7/2001 | Warthoe |
| 6,261,775 B1 | 7/2001 | Bastian et al. |
| 6,268,142 B1 | 7/2001 | Duff et al. |
| 6,268,184 B1 | 7/2001 | Gray et al. |
| 6,277,563 B1 | 8/2001 | Shayesteh et al. |
| 6,280,929 B1 | 8/2001 | Gray et al. |
| 6,280,935 B1 | 8/2001 | Macevicz |
| 6,280,950 B1 | 8/2001 | Lipshutz et al. |
| 6,287,778 B1 * | 9/2001 | Huang ................ C12Q 1/6827 435/5 |
| 6,306,643 B1 | 10/2001 | Gentalen et al. |
| 6,309,822 B1 | 10/2001 | Fodor et al. |
| 6,322,971 B1 | 11/2001 | Chetverin et al. |
| 6,322,985 B1 | 11/2001 | Kashi et al. |
| 6,326,148 B1 | 12/2001 | Pauletti et al. |
| 6,335,167 B1 | 1/2002 | Pinkel et al. |
| 6,344,316 B1 | 2/2002 | Lockhart et al. |
| 6,352,828 B1 | 3/2002 | Brenner |
| 6,355,431 B1 | 3/2002 | Chee et al. |
| 6,358,683 B1 | 3/2002 | Collins |
| 6,361,947 B1 | 3/2002 | Dong et al. |
| 6,365,352 B1 | 4/2002 | Yerramilli et al. |
| 6,365,353 B1 | 4/2002 | Loerch et al. |
| 6,432,648 B1 | 8/2002 | Blumenfeld et al. |
| 6,444,426 B1 | 9/2002 | Short et al. |
| 6,451,529 B1 | 9/2002 | Jensen et al. |
| 6,455,258 B2 | 9/2002 | Bastian et al. |
| 6,455,280 B1 | 9/2002 | Edwards et al. |
| 6,465,180 B1 | 10/2002 | Bastian et al. |
| 6,465,182 B1 | 10/2002 | Gray et al. |
| 6,468,742 B2 | 10/2002 | Nerenberg, I et al. |
| 6,468,744 B1 | 10/2002 | Cronin et al. |
| 6,475,732 B1 | 11/2002 | Shayesteh et al. |
| 6,479,242 B1 * | 11/2002 | Guo ................ C12Q 1/6872 435/6.11 |
| 6,500,612 B1 | 12/2002 | Gray et al. |
| 6,509,160 B1 | 1/2003 | Sapolsky et al. |
| 6,521,428 B1 | 2/2003 | Senapathy |
| 6,532,648 B2 | 3/2003 | Murakami et al. |
| 6,534,293 B1 | 3/2003 | Barany et al. |
| 6,562,565 B1 | 5/2003 | Pinkel et al. |
| 6,596,479 B1 | 7/2003 | Gray et al. |
| 6,617,137 B2 | 9/2003 | Dean et al. |
| 6,664,057 B2 | 12/2003 | Albertson et al. |
| 6,703,228 B1 | 3/2004 | Landers et al. |
| 6,720,179 B1 | 4/2004 | Macevicz |
| 6,773,885 B1 | 8/2004 | Walder et al. |
| 6,773,886 B2 | 8/2004 | Kaufman et al. |
| 6,777,187 B2 | 8/2004 | Makarov et al. |
| 6,812,005 B2 | 11/2004 | Fan et al. |
| 6,812,339 B1 | 11/2004 | Venter et al. |
| 6,818,394 B1 | 11/2004 | O'Donnell-Maloney et al. |
| 6,872,529 B2 | 3/2005 | Su |
| 7,094,534 B2 | 8/2006 | Pinkel et al. |
| 7,108,976 B2 | 9/2006 | Jones et al. |
| 7,153,687 B2 | 12/2006 | Yu et al. |
| 7,267,966 B2 | 9/2007 | Dong et al. |
| 7,297,778 B2 | 11/2007 | Matsuzaki et al. |
| 7,459,273 B2 | 12/2008 | Jones et al. |
| 7,582,420 B2 | 9/2009 | Oliphant et al. |
| 7,588,889 B2 | 9/2009 | Wolber et al. |
| 8,854,033 B2 | 10/2014 | Shiraki et al. |
| 9,388,459 B2 | 7/2016 | Shapero |
| 2001/0034023 A1 | 10/2001 | Stanton et al. |
| 2002/0042112 A1 * | 4/2002 | Koster ................ B01J 19/0046 435/174 |
| 2002/0127561 A1 | 9/2002 | Bee et al. |
| 2002/0165345 A1 | 11/2002 | Cohen et al. |
| 2003/0036069 A1 | 2/2003 | Su |
| 2003/0186280 A1 | 10/2003 | Kennedy |
| 2003/0232348 A1 | 12/2003 | Jones et al. |
| 2004/0033496 A1 | 2/2004 | Yu et al. |
| 2004/0110153 A1 | 6/2004 | Dong et al. |
| 2004/0137473 A1 | 7/2004 | Wigler et al. |
| 2004/0259100 A1 | 12/2004 | Gunderson et al. |
| 2005/0032102 A1 | 2/2005 | Shigeta |
| 2005/0042654 A1 | 2/2005 | Mei et al. |
| 2005/0095645 A1 | 5/2005 | Jones et al. |
| 2005/0100911 A1 | 5/2005 | Patil et al. |
| 2005/0148004 A1 | 7/2005 | Wolber et al. |
| 2006/0063158 A1 | 3/2006 | Dong et al. |
| 2006/0068415 A1 | 3/2006 | Jones et al. |
| 2006/0073501 A1 | 4/2006 | Van Den Boom et al. |
| 2006/0073511 A1 | 4/2006 | Jones et al. |
| 2006/0134674 A1 | 6/2006 | Huang et al. |
| 2006/0246457 A1 | 11/2006 | Dirks et al. |
| 2007/0031858 A1 * | 2/2007 | Makarov ............... C12Q 1/6846 435/6.12 |
| 2007/0048756 A1 | 3/2007 | Mei et al. |
| 2007/0065816 A1 | 3/2007 | Dong et al. |

FOREIGN PATENT DOCUMENTS

| | | |
|---|---|---|
| EP | 1621474 | 2/2006 |
| EP | 1645640 A2 | 4/2006 |
| WO | WO-9008821 A1 | 8/1990 |
| WO | WO-9641893 A1 | 12/1996 |
| WO | WO-9710365 A1 | 3/1997 |
| WO | WO-9923256 A1 | 5/1999 |
| WO | WO-0023620 A1 | 4/2000 |
| WO | WO-0024939 A1 | 5/2000 |
| WO | WO-0078975 A2 | 12/2000 |
| WO | WO0101106 | 1/2001 |
| WO | 01/38580 A2 | 5/2001 |
| WO | WO-0188174 A1 | 11/2001 |
| WO | WO-03010328 A2 | 2/2003 |
| WO | WO-03033724 A2 | 4/2003 |
| WO | WO-03106642 A2 | 12/2003 |
| WO | WO-2004058945 A2 | 7/2004 |
| WO | WO-2006097462 A2 | 9/2006 |

OTHER PUBLICATIONS

Zhang, J. & Li, K. Single-Base Discrimination Mediated by Proofreading 3' Phosphorothioate-Modified Primers. Molecular Biotechnology 2003; 25: 223-227. (Year: 2003).*

O'Meara et al. SNP typing by apyrase-mediated allele-specific primer extension on DNA microarrays. Nucleic Acids Research 2002; 30: e75. (Year: 2002).*

Gunderson et al. A genome-wide scalable SNP genotyping assay using microarray technology. Nature Genetics 2005; 37: 549-554. (Year: 2005).*

Gunderson et al. Decoding Randomly Ordered DNA Arrays. Genome Research 2004; 14: 870-877. (Year: 2004).*

Agbo et al., "Molecular variation of *Trypanosoma brucei* subspecies as revealed by AFLP fingerprinting," Parasitology, vol. 124, No. 4, pp. 349-358 (Apr. 2002).

Bohling et al., "Rapid simultaneous amplification and detection of the MBR/JR chromosomal translocation by fluorescence melting curve analysis," Amer. J. Pathol., 154:97-103(1999).

Broude et al., High Level Mulitplex DNA Amplification; Antisense & Nucleic Acid Drug Development, 2001, 11: 327-332.

(56) References Cited

OTHER PUBLICATIONS

Broude et al., "Multiplex Allele-Specific Target Amplification Based on PCR Suppression," PNAS, vol. 98, No. 1, pp. 206-211 (Jan. 2001) . . . .

Buckley et al., A Full-coverage, High-resolution Human Chromosome 22 Genomic Mircroarray for Clinical and Research Applications. Human Molecular Genetics, 2002, 3221-3229, vol. 11(5).

Craig et al., "Removal of repetitive sequences from FISH probes using PCR-assisted Affinity Chromotography," Human Genetics, vol. 100, No. 3-4, pp. 472-476 (1997).

Cutler et al., "High-throughput variation detection and genotyping using microarrays," Genome Research, vol. 11, No. 11, 1913-1925 (Nov. 2001).

De Noronha, C.M. et al., "Amplimers with 3'-terminal phosphorothioate linkages resist degradition by vent polymerase and reduce Taq polymerase mispriming", Genome Research, vol. 2, 1992, 131-136.

Dhulipala et al., "GenomiPhi amplification of human genomic DNA: utility of amplified; DNA in genetic variation experiments," 2003 FASEB Meeting on Experimental; Biology: Translating the Genome, San Diego, CA, Apr. 11-15, 2003, FASEB Journal, vol. 17, No. 4-5, Abstract No. 371.3 {2003};.

DiGusto et al., "Strong positional preference in the interaction of LNA oligonucleotides; with DNA polymerase and proofreading exonuclease activities: implications for; genotyping assays," Nucleic Acids Research, 32{3}: e32 {2004} ;.

Draghici, "Statistical intelligence: effective analysis of high-density microarray data," Drug Discovery Today, vol. 7, pp. S55-S63 (Jun. 2002).

Dumar et al., "Genome-wide detection of LOH in prostate cancer using human SNP microarray technology," Genomics, 2003, vol. 81, Issue 3, pp. 260-269.

Durm et al., Fast-painting of Human Metaphase Spreads Using a Chromosome-Specific, Repeat-Depleted DNA Library Probe; Biotechniques, Eaton Publishing; Vo. 24; No. 5; May 1988; pp. 820-825.

Fan et al., "Parallel Genotyping of Human SNP's Using Generic High-Density Oligonucleotide Tag Arrays," Genome Research, vol. 10, pp. 853-860, (2000).

Huang et al. Multiple Cleavage Activities of Endonuclease V from Thermotoga maritima: Recognition and Strand Nicking Mechanism. Biochemistry (2001) 40: 8738-8748.

Huang et al., "Whole genome DNA copy number changes identified by high density oligonucleotide arrays," Human Genomics, vol. 1, No. 4, pp. 287-299 (May 2004).

Ji et al. Single-Step Assays to Analyze CYP2D6 Gene Polymorphisms in Asians: Allele Frequencies and a Novel 14B Allele in Mainland Chinese. Clinical Chemistry (2002) 48(7): 983-988.

Kallioniemi et al., "Comparative Genomic Hybridization for Molecular Cytogenetic Analysis of Solid Tumors," Science, 1992, vol. 258, No. 5083, pp. 818-821.

Kaminski et al., "Practical Approaches to Analyzing Results of Microarray; Experiments," American Journal of Respiratory Cell and Molecular Biology, vol. 27,; pp. 125-132 {Aug. 2002};.

Kennedy et al., "Large-scale Genotyping of Complex DNA," Nature Biotechnology, vol. 21(10), pp. 1233-1237 (Oct. 2003).

Klein, C. A. et al. "Comparative genomic hybridization, loss of heterozygosity, and DNA sequence analysis of single cells," Proc. Nati.Acad.Sci.U.S.A, vol. 96, Apr. 13, 1999, pp. 4494-4499.

Laan, et al., Solid-phase minisequencing confirmed by Fish analysis in determination of gene copy number, Human Genetics, 96(3), 275-80, 1995.

Lindblad-Toh et al., "Loss-of-Heterozygosity Analysis of Small-Cell Lung Carcinomas Using Single-Nucleotide Polymorphism Arrays," Nature Biotechnology, vol. 18, pp. 1001-1005, (2000).

Lindstedt et al., "A variation of the amplified-fragment length polymorphism {AFLP}; technique using three restriction endonucleases, and assessment of the enzyme; combination Bgiii-Mfel for AFLP analysis of *Salmonella enterica* subsp. *enterica*; isolates," FEMS Microbiology Letters, Aug. 2000, vol. 189, No. 1, pp. 19-24;.

Liu et al., "Physical and genetic mapping of the macular corneal dystrophy locus on chromosome 16q and exclusion of TAT and LCAT as candidate genes," Molecular Vision, vol. 6, pp. 95-100, (2000).

Lovmar et al., "Quantitative evaluation by minisequencing and microarrays reveals accurate multiplexed SNP genotyping of whole genome amplified DNA," Nucleic Acids Research, 31(21):e129, pp. 1-9 (2003).

Lucito et al., "Detecting Gene Copy Number Fluctuations in Tumor Cells by Microarray Analysis of Genomic Representations," Genome Research, 1726-1736, vol. 10(11) (2000).

Lucito et al., "Genetic Analysis Using Genomic Representations," Proc. National Academy of Sciences, vol. 95, pp. 4487-4492 (Apr. 1998).

Lucito, R. et al. "Representational oligonucleotide microarray analysis: a high-resolution method to detect genome copy number variation," Genome Res., vol. 13, Oct. 2003, pp. 2291-2305.

Marenstein et al., Human AP endonuclease (APE1) demonstrates endonucleolytic activity against AP sites in single-stranded DNA, Elsevier, DNA Repair 3 (2004), 527-533.

Matsuzaki et al., "Genotyping of over 100,000 SNPs on a pair of oligonucleotide arrays," Nature methods 1 (2) : 109-111 (2004).

Matsuzaki et al., "Parallel genotyping of over 10,000 SNPs using a one-primer assay; on a high-density oligonucleotide array," Genome Research 14: 414-425 {2004};.

McDonald et al., "Molecular haplotyping of genomic DNA for multiple single nucleotide; polymorphisms located kilobases apart using long range polymerase chain reaction; and intramolecular ligation," Pharmacogenetics, vol. 12, No. 2, Feb. 2002, pp. 93-99;.

Mei et al., Genome-wide Detection of Allelic Imbalance Using Human SNPs and High-density DNA Arrays. Genome Research. 2000, 1126-1137, vol. 10 (8).

Mitra et al., "Localization of cancer susceptibility genes by genome-wide single-nucleotide polymorphism linkage-disequilibrium mapping," Cancer Research 64: 8116-8125 (Nov. 2004).

Mohapatra, G. et al. "Analyses of brain tumor cell lines confirm a simple model of relationships among fluorescence in situ hybridization, DNA index, and comparative genomic hybridization," Genes Chromosomes.Cancer, vol. 20, Dec. 1997, pp. 311-319.

Olejnik et al., "Photocleavable biotin phosphoramidite for 5'-end-labeling, affinity; purification and phosphorylation of synthetic oligonucleotides," Nucleic Acids Res.; (1996) 24:361-366;.

Paez et al., "Genome coverage and sequence fidelity of .PHI.29 polymerase-based multiple strand displacement whole genome amplification," Nucleic Acids Research, 32(9), e71, pp. 1-11 (2004).

Pinkel, D. et al. "High resolution analysis of DNA copy number variation using comparative genomic hybridization to microarrays," Nat. Genet., vol. 20, Oct. 1998, pp. 207-211.

Pollack et al., "Microarray Analysis Reveals a Major Direct Role of DNA Copy Number Alterations in the transcriptional Program of Human Breast Tumors," Proceedings of the National Academy of Sciences,Oct. 2002, vol. 99, No. 20, pp. 12963-12968_.

Schubert et al., "Single Nucleotide Polymorphism Array Analysis of Flow-Sorted Epithelial Cells from Frozen Versus Fixed Tissues for Whole Genome Analysis of Allelic Loss in Breast Cancer," Am. J. Pathol., vol. 160, pp. 73-79 (2002).

Sebat et al., "Large-Scale Copy Number Polymorphism in the Human Genome," Science, 2004, vol. 305, pp. 525-528.

Shi, "Enabling large-scale pharmacogenetic studies by high-throughput mutation detection and genotyping technologies," Clinical Chemistry, vol. 47, No. 2, Feb. 2000, pp. 164-172.

Siebert et al., "An Improved PCR Method for Walking an Uncloned Genomic DNA," Nucleic Acids Research, vol. 23, No. 6, pp. 1087-1088 (1995).

Snijders et al., "Assembly of Microarrays for Genome-wide Measurement of DNA Copy Number," Nature Genetics, vol. 29, pp. 263-264 (2001).

Stratagene Catalog (1988), p. 39. Published by Stratgene, 11011 North Torrey Pines Road, La Jolla, CA 92037, USA.

Tzvetkov et al., "Genome-wide single-nucleotide polymorphism arrays demonstrate high fidelity of multiple displacement-based whole-genome amplification," Electrophoresis, vol. 26, No. 3, Feb. 2005, pp. 710-715.

(56) References Cited

OTHER PUBLICATIONS

Van Der Wurff et al., "TE-AFLP combining rapidity and robustness in DNA fingerprinting," Nucleic Acids Research, vol. 28, No. 24, e105 (Dec. 2000).
Vos et al., "AFLP: A New Technique for DNA Fingerprinting," Nucleic Acids Research, vol. 23, No. 21, pp. 4407-4414 (1995) . . . .
Wang et al., "Construction and characterization of a human chromosome 2-specific BAC library," Genomics, vol. 24, pp. 527-534, 1994.
Wang, et al., "Large-Scale Identification, Mapping, and Genotyping of Single-Nucleotide Polymorphisms in the Human Genome", Science, 280:, 1998, 1077-1082.
Wodicka et al., "Genome-wide expression monitoring in *Saccharomyces cerevisiae*," Nature Biotechnology, vol. 15, pp. 1359-1367 (1997).
Xiang et al., "A Huntington disease-like neurodegenerative disorder maps to chromosome 20p," American Journal of Human Genetics, vol. 63, 1998, pp. 1431-1438.
Ye et al. Fluorescent Microsphere-Based Readout Technology for Multiplexed Human Single Nucleotide Polymorphism Analysis and Bacterial Identification. Human Mutation (2001) 17:305-316.
Zhou et al., "Match-Only Integral Distribution (MOID) Algorithm for high-density oligonucleotide array analysis," BMC Bioinformatics, vol. 3, No. 3 Article 3 (Jan. 2002), pp. 1-15.
Hatch et al. Genetic Analysis: Biomolecular Engineering 15: 35-40 (1999).
International Search Report received for PCT Patent Application No. PCT/US2003/018853, dated Aug. 20, 2004, 2 pages.
Shoemaker et al. Nature 409: 922-927 (2001).

* cited by examiner

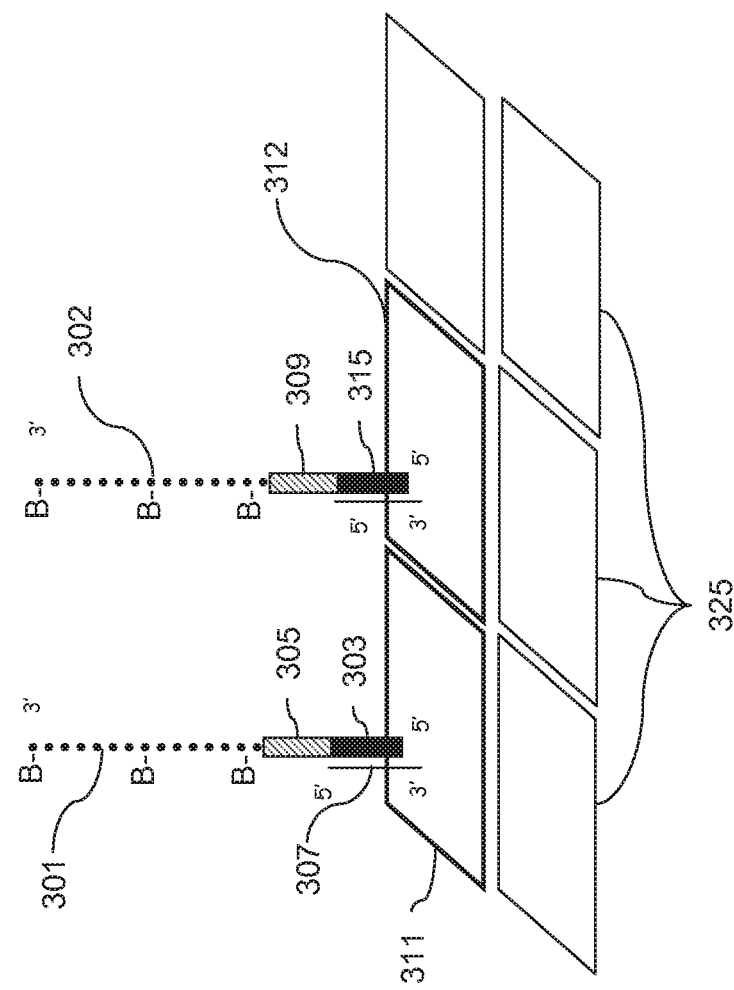

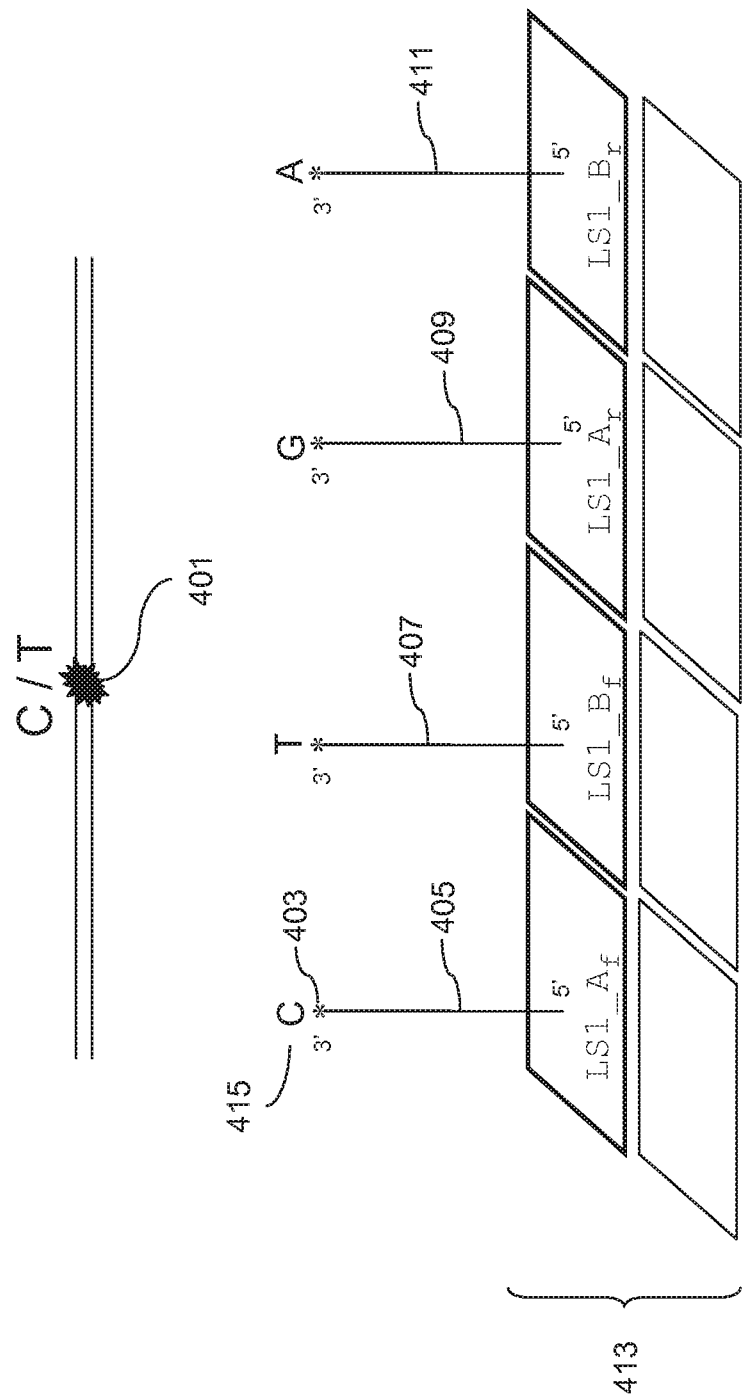

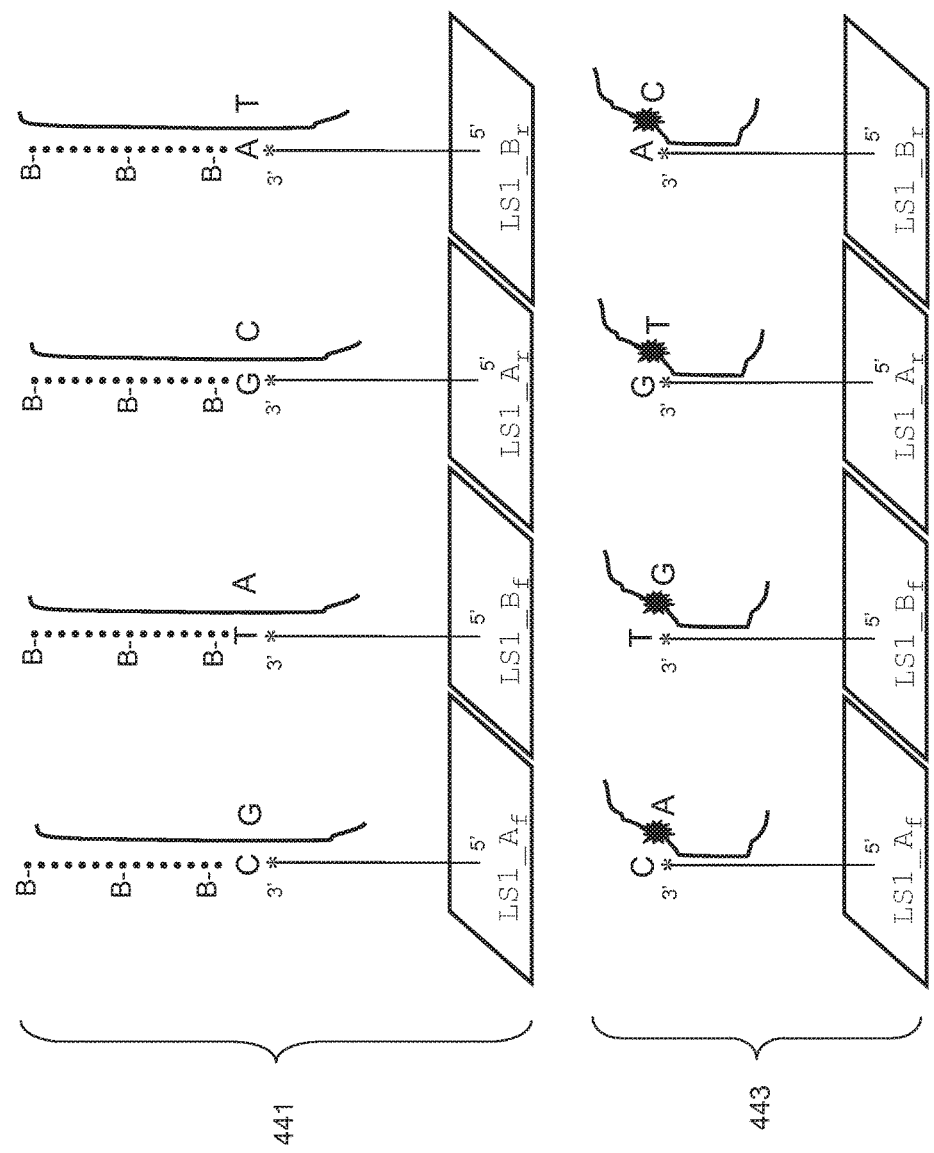

METHODS FOR GENOTYPING

RELATED APPLICATIONS

This application is a continuation application of U.S. application Ser. No. 15/184,469 filed on Jun. 16, 2016 and now abandoned, which is a continuation application of U.S. application Ser. No. 11/614,948, filed on Dec. 21, 2006 now U.S. Pat. No. 9,388,459, which claims the benefit of U.S. Provisional Application No. 60/752,782 filed Dec. 21, 2005, each of which are hereby incorporated by reference in their entireties.

FIELD OF THE INVENTION

The invention relates to methods for determining the genotype of one or more polymorphisms using allele specific primer extension.

BACKGROUND OF THE INVENTION

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, Alzheimer disease or alcoholism, Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3 \times 10^9$ base pairs. Novel methods of sample preparation and sample analysis that reduce complexity may provide for the fast and cost effective exploration of complex samples of nucleic acids, particularly genomic DNA.

Single nucleotide polymorphisms (SNPs) have emerged as the marker of choice fix genome wide association studies and genetic linkage studies. Building SNP maps of the genome will provide the framework for new studies to identify the underlying genetic basis of complex diseases such as cancer, mental illness and diabetes as well as normal phenotypic variation. Due to the wide ranging applications of SNPs there is a continued need for the development of increasingly robust, flexible, and cost-effective technology platforms that allow for genotype scoring of many polymorphisms in large numbers of samples.

Allele specific primer extension is one method of analysis of point imitations (Newton et al., *Nucleic Acids Res.*, 17, 2503-2516 (1989). For SNP genotyping the method uses two allele-specific extension primers that differ in their 3'-positions. Each Is primer matches one allele perfectly but has a 3' mismatch with the other allele. The DNA polymerase has much higher extension efficiency for the perfect match than for the mismatch.

SUMMARY OF THE INVENTION

The present invention provides for novel methods of sample preparation and analysis comprising managing or reducing the complexity of a nucleic acid sample by amplification of a collection of target sequences using target specific capture probes. In some embodiments the extended capture probes are attached to a solid support such as beads; in some embodiments the extended capture probes are attached to an array. In some embodiments the amplified collection of target sequences is analyzed by hybridization to an array that is designed to interrogate sequence variation in the target sequences. In some embodiments the amplified collection of target sequences is analyzed by hybridization to an array of tag probes.

In one embodiment a method of generating a collection of target sequences from a nucleic acid sample is disclosed. The nucleic fragment is fragmented to generate a plurality of fragments. A collection of capture probes is hybridized to the fragments wherein the capture probes are attached to a solid support at a 5'end and comprise a spacer sequence near the 5 end, multiple dU residues, a tag sequence for each species of capture probe, a target sequence, and the 3' end of the capture probes terminates with a specific nucleotide corresponding to the polymorphism. The capture probes are extended in the presence of one or more DNA polymerase. The solid support is washed to remove the fragments. The extended capture probes are cleaved from the solid support via photo or enzymatic cleavage. The tag sequence of the extended capture probes is hybridized to an array comprising a plurality of tag probes. The target sequences are generated containing the polymorphism on the solid support.

In some embodiments the capture probes are attached to the solid support through a covalent interaction. In another embodiment the solid support comprises a plurality of beads. In some embodiments the beads further comprises anti-digoxigenin, thereby capturing the capture probes with a digoxigenin label at the 5' end.

In another embodiment the DNA polymerase has a 3' to 5' Exonuclease proofreading activity (e.g., VENT® or DEEP VENT® DNA polymerases). In some embodiments the DNA polymerase comprises a mesophilic polymerase. In another embodiment, the DNA polysmerase comprises Taq GOLD™ (a modified Taq polymerase requiring thermal activation), VENT®, DEEP VENT®, T4 DNA Polymerase, *E. Coli* Klenow fragment, and T7 DNA polymerase. In some embodiments, the beads are washed with 0.15N NaOH to remove fragments of the nucleic acid sample.

In another embodiment the enzymatic cleavage of the extended capture probes from the solid support uses an endonuclease. In some embodiments the endonuclease comprises uracil DNA glycosylase (UDG). In another embodiment, the enzymatic cleavage of the extended capture probes from the solid support is by heat. In some embodiments, the photo cleavage is accomplished by UV light. In another embodiment, the UV light has a wavelength is between 200 and 400 nanometers.

In some embodiments, in each extension reaction there is at least one species of labeled dNTP. In another embodiment, one or more species of dNTPs is labeled with biotin. In some embodiment, the labeled nucleotides are incorporated into the extended capture probes. In another embodiment there is one extension reaction wherein four differentially labeled dNTPs are present in the extension reaction.

In some embodiments the capture probes are extended on a solid support in a 5' to 3' direction. In another embodiment the spacer sequence comprise a run of 2 to 12 T residues. In some embodiments the dU region comprises UIUI and UIUIUI. In another embodiment, Endonuclease V cleaves dI residues. In some embodiments, the 3' end of the capture probes comprises 0, 1, 2 or 3 phosphorothioate linkages.

In another embodiment, a method for genotyping one or more polymophisms in a nucleic acid sample is disclosed. A collection of target sequences from the sample is generated. The collection of target sequences is hybridized to an array comprising a plurality of tag probes that hybridize to the tag sequences in the extended capture probes. The hybridization pattern is analyzed on each of the arrays to determine at least one genotype.

In one embodiment, a method of generating a collection of target sequences containing one or more polymorphisms from a nucleic acid sample is disclosed. A collection of capture probes is synthesized comprising a plurality of different species of primers wherein a 5' end of the collection of capture probe is attached to a solid support and a 3' variable region is specific for a target sequence in the collection target sequences and terminates with a specific nucleotide corresponding to the polymorphism. The nucleic acid sample is amplified with a whole genome amplification method. The nucleic acid sample is fragmented to generate fragments. The fragments are hybridized to the collection of capture probes on a solid support. The solid support is washed to remove the fragments. The target sequences containing the polymorphism are generated by extending the capture probes using DNA polymerases.

In some embodiments, the whole genome amplification method comprises MDA and Omniplex. In another embodiment the primer extension reaction comprises full or partial substitution of one or more labeled dNTPs. In some embodiments, the polymorphism comprises a SNP.

In another embodiment a method of genotyping one or more polymorphic locations in a sample is disclosed. A collection of target sequences from the sample is generated. The collection of target sequences is hybridized to an array designed to interrogate at least one polymorphic location in the collection of target sequences. The hybridization pattern is analyzed to determine the identity of an allele or alleles present at one or more polymorphic location in the collection of target sequences.

BRIEF DESCRIPTION OF THE FIGURES

FIG. 3 shows a method of detection of tagged extension products on an array of tag probes.

FIG. 4A shows an array of allele specific probes with nuclease resistant linkages at the 3' ends of the probes.

FIG. 4D shows extension of the allele specific probes with a perfect match at the 3' end and absence of extension of allele specific probes with a mismatch at the 3' end.

Figure 1:
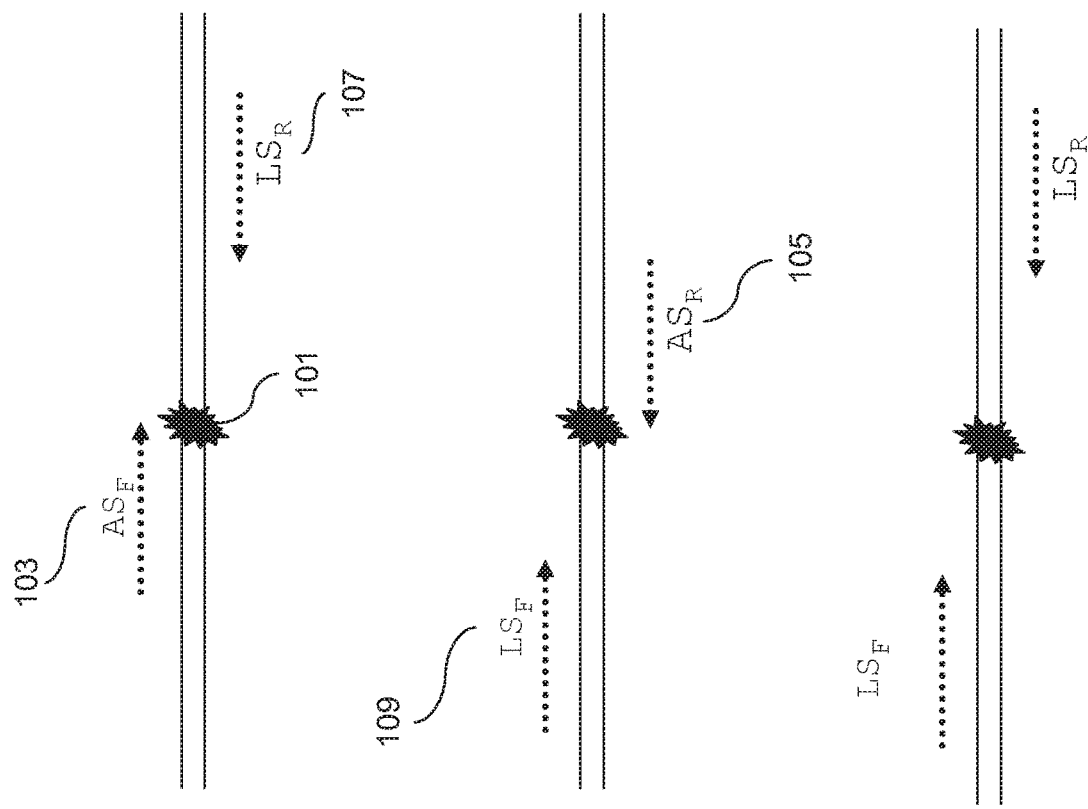
FIG. 1 shows a schematic of allele specific primer extension. Allele specific primers may be designed to hybridize to either strand.

DETAILED DESCRIPTION OF THE PREFERRED EMBODIMENTS a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range, For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. The same holds true for ranges in increments of $10^5$, $10^4$, $10^3$, $10^2$, 10, $10^{-1}$, $10^{-2}$, $10^{-3}$, $10^{-4}$, or $10^{-5}$, for example. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer (anyone have the cite), Gait, "*Oligonucleotide Synthesis: A Practical Approach*" 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y. all of which are herein incorporated in their entirety by reference for all purposes.

The present invention can employ solid substrates, including arrays in some preferred embodiments. Methods and techniques applicable to polymer (including protein) synthesis have been described in U.S. Patent Publication No. 20050074787, International Publication No. WO 00/58516, U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US 01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165 and 5,959,098 which are each incorporated herein by reference in their entirety for all purposes. Nucleic acid arrays are described in many of the above patents, but the same techniques are applied to polypeptide arrays.

The present invention also contemplates many uses for polymers attached to solid substrates. These uses include gene expression monitoring, profiling, library screening, genotyping, and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Pat. Nos. 5,856,092, 6,300,063, 5,858,659, 6,284,460, 6,361,947, 6,368,799, 6,333,179 and 6,872,529 which are each incorporated herein by reference. Other uses are embodied in U.S. Pat. Nos. 5,871,928, 5,902,723, 6,045,996, 5,541,061, and 6,197,506 which are incorporated herein by reference.

The present invention also contemplates sample preparation methods in certain preferred embodiments. For example, see the patents in the gene expression, profiling, genotyping and other use patents above, as well as U.S. Pat. Nos. 6,582,938, 5,437,990, 5,215,899, 5,466,586, and 4,357,421, and Gubler et al., 1985, *Biochemica et Biophysica Acta*, Displacement Synthesis of Globin Complementary DNA: Evidence for Sequence Amplification.

Prior to or concurrent with analysis, the nucleic acid sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Manila. et al. *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, each of which is incorporated herein by reference in their entireties for all purposes. The sample may be amplified on the array. See, for example, U.S. Pat. No. 6,300,070 which is incorporated herein by reference.

Other suitable amplification methods include the ligase chain reaction (LCR) (e.g., Wu and Wallace, *Genomics* 4, 560 (1989), Landegren et al, *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990), WO/88/10315 and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), degenerately primed PCR (DOP-PCR) (See, Telenius et al. *Genomics* 13: 718-725, 1992 and Cheung and Nelson *Proc. Natl. Acad. Sci.* 93: 14676-14679, 1996), primer extension PCR (PEP) (See, Zhang, et al. *Proc. Natl. Acad. Sci.* 89: 5847-5851, 1992), and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 6,582,938, 5,242,794, 5,494,810, and 4,988,617, each of which is incorporated herein by reference. In preferred aspects, the sample may be amplified using multiple-displacement amplification (MDA) or OMNIPLEX amplification. MDA uses a highly processive DNA polymerase and random exonuclease resistant primers in an isothermal amplification reaction (Dean et al., *Proc. Natl. Acad. Sci.* 99: 5261-5266, 2002). The method is based on strand displacement synthesis and generally results in products that are greater than 10 kb in length. The OMNIPLEX amplification method uses random fragmentation of the DNA to form a library of fragments of defined size. The fragments can be amplified using a DNA polymerase (Langmore, *Pharmacogenomics* 3:557-60, 2002 and US Patent Pub. No. 20030040620).

Additional methods of sample preparation and techniques for reducing the complexity of a nucleic sample are described in Dong et al., *Genome Research* 11, 1418 (2001), in U.S. Pat. Nos. 6,300,070, 6,361,947, 6,391,592, 6,958,225, 6,632,611 and 6,872,529 and U.S. Patent Pub. No. 20050260628, which are incorporated herein by reference in their entireties.

The present invention also contemplates detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Methods for analysis of genotype using array data are described, for example, in Di, X., et al. (2005) *Bioinformatics,* 21, 1958-1963, Liu, W., et al. (2003) *Bioinformatics,* 19, 2397-2403 and Rabbee and Speed (2006) *Bioinformatics* 22:7-12. Methods for copy number analysis based on hybridization to arrays of oligonucleotides have been disclosed, for example, in US Patent Pub. Nos. 20040157243, 20060134674, 20050130217, and 20050064476.

Additionally, the present invention may have preferred embodiments that include methods for providing genetic information over networks such as the Internet as shown in U.S. Patent applications 20020183936, 20030100995, 20030120432, 20040002818, and 20040049354.

The present invention provides a flexible and scalable method for analyzing complex samples of nucleic acids, such as genomic. DNA. These methods are not limited to any particular type of nucleic acid sample: plant, bacterial, animal (including human) total genome DNA, RNA, cDNA and the like may be analyzed using some or all of the methods disclosed in this invention. The word "DNA" may be used below as an example of a nucleic acid. It is understood that this term includes all nucleic acids, such as DNA and RNA, unless a use below requires a specific type of nucleic acid. This invention provides a powerful tool for analysis of complex nucleic acid samples. From experimental design to isolation of desired fragments and hybridization to an appropriate array, the invention provides for fast, efficient and inexpensive methods of complex nucleic acid analysis.

b) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

A genome is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 1.0^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

Polymorphism refers to the occurrence of two or more genetically determined alternative sequences or alleles in a population. A polymorphic marker or site is the locus at which divergence occurs. Preferred markers have at least two alleles, each occurring at frequency of preferably greater than 1%, and more preferably greater than 10% or 20% of a. selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VN-TR's), hypervariable regions, minisatellites, dinucleotide repeats, trinucleotide repeats, tetranucleotide repeats, simple sequence repeats, insertion elements such as Alu or small insertions or deletions, for example, deletions or insertions of 1-10 bases. The first identified allelic form is arbitrarily designated as the reference form and other allelic farms are designated as alternative or variant alleles. The allelic form occurring most frequently in a selected population is sometimes referred to as the wild type form. Diploid organisms may be homozygous or heterozygous for allelic forms. When an organism carries two identical alleles the organism is homozygous at that position. When an organism carries two different alleles the organism is heterozygous at that position. Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

Single nucleotide polymorphisms (SNPs) are positions at which two alternative bases occur at appreciable frequency (generally greater than 1%) in the human population, and are the most common type, of human genetic variation. The site is usually preceded by and followed by highly conserved sequences of the allele (e.g., sequences that vary in less than $\frac{1}{100}$ or $\frac{1}{1000}$ members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A diallelic polymorphism has two forms in a population. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

The design and use of allele-specific probes for analyzing polymorphisms is described by e.g., Saiki et al., *Nature* 324, 163-166 (1986); Dattagupta, E P 235,726, Saiki, and WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles.

The term "linkage" as used herein describes the tendency of genes, alleles, loci or genetic markers to be inherited together as a result of their location on the same chromosome. Linkage can be measured in various ways.

"Linkage disequilibrium", or LD", as used herein, refers to the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium.

Linkage disequilibrium may result from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

Linkage can be analyzed by calculation of LOD (log of the odds) values. A lod value is the relative likelihood of obtaining observed segregation data for a marker and a genetic locus when the two are located at a recombination fraction ($\theta$), versus the situation in which the two are not linked, and thus segregating independently (Thompson & Thompson, Genetics in Medicine (5th ed, W. B. Saunders Company, Philadelphia, 1991); Strachan, "Mapping the human genome" in The Human Genome (BIOS Scientific Publishers Ltd, Oxford), Chapter 4). A series of likelihood ratios are calculated at various recombination fractions ($\theta$), ranging from $\theta=0.0$ (coincident loci) to $\theta=0.50$ (unlinked). Thus, the likelihood at a given value of $\theta$ is: probability of data if loci linked at $\theta$ to probability of data if loci unlinked. The computed likelihoods are usually expressed as the log 10 of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of $\theta$ (e.g., LIPED, MLINK (Lathrop, *Proc. Nat. Acad. Sci.* (USA) 81:3443-3446 (1984)) For any particular lod score, a recombination fraction may be determined from mathematical tables. See Smith et al., Mathematical tables for research workers in human genetics (Churchill, London, 1961); Smith, Ann. Hum. Genet. 32:127-150 (1968). The value of $\theta$ at which the lod score is the highest is considered to be the best estimate of the recombination fraction.

Positive lod score values suggest that the two loci are linked, whereas negative values suggest that linkage is less likely (at that value of .theta.) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. Negative linkage data are useful in excluding a chromosome a segment thereof from consideration. The search focuses on the remaining non-excluded chromosomal locations.

Statistical and computational methods for mapping of complex traits are disclosed, for example, in McKeigue et al., Am. J. Hum. Genet, 76:1-7 (2005), Lander and Shork, Science 265:2037-2048 (1994), McKeigue, Am. J. Hum. Genet 63:241-251 (1998), and Patterson et al., Am. J. Hum. Genet. 74:979-1000 (2004).

Capture probes are oligonucleotides that have a 5' common sequence and a 3' locus or target specific region or primer. The locus or target specific region is designed to hybridize near a region of nucleic acid that includes a region of interest so that the locus or target specific region of the capture probe can be used as a primer and be extended through the region of interest to make a copy of the region of interest. The common sequence in the capture probe may be used as a priming site in subsequent rounds of amplification using a common primer or a limited number of common primers. The same common sequence may be present in many or all or the capture probes in a collection of capture probes. Capture probes may also comprise other sequences, for example, tag sequences that are unique for different species of capture probes, and endonuclease recognition sites.

A tag or tag sequence is a selected nucleic acid with a specified nucleic acid sequence. A tag probe has a region that is complementary to a selected tag. A set of tags or a collection of tags is a collection of specified nucleic acids that may be of similar length and similar hybridization properties, for example similar $T_m$. The tags in a collection of tags bind to tag probes with minimal cross hybridization so that a single species of tag in the tag set accounts for the majority of tags which bind to a given tag probe species under hybridization conditions. For additional description of tags and tag probes and methods of selecting tags and tag probes see U.S. Pat. No. 6,458,530 and EP 0799897, each of which is incorporated herein by reference in their entirety. See also U.S. patent application Ser. No. 09/827,383.

A collection of capture probes may be designed to interrogate a collection of target sequences. The collection would comprise at least one capture probe for each target sequence to be amplified and preferably one capture probe for each allele of each polymorphism being interrogated. There may be multiple different capture probes for a single target sequence in a collection of capture probes, for example, there may be a capture probe that hybridizes to one strand of the target sequence and a capture probe that hybridizes to the opposite strand of the target sequence, these may be referred to as a forward locus or target specific primer and a reverse locus or target specific primer. In preferred embodiments the capture probes have a region that is complementary to the region immediately 3' of the polymorphic position and a base that is complementary to the polymprphism. Capture probes may also have additional sequences 5' of the target complementary region, for example, a tag sequence, one or more priming sequences (may be common to multiple capture probes), or a restriction site.

The term "target sequence", "target nucleic acid" or "target" refers to a nucleic acid of interest. The target sequence may or may not be of biological significance. As non-limiting examples, target sequences may include regions of genomic DNA which are believed to contain one or more polymorphic sites, DNA encoding or believed to encode genes or portions of genes of known or unknown function, DNA encoding or believed to encode proteins or portions of proteins of known or unknown function, and DNA encoding or believed to encode regulatory regions such as promoter sequences, splicing signals, polyadenylation signals, etc. The number of sequences to be interrogated can vary, but preferably are from about 1000, 2,000, 5,000, 10,000, 20,000 or 100,000 to 5000, 10,000, 100,000, 1,000,000 or 3,000,000 target sequences.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., Science, 251:767-777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. See U.S. Pat. Nos. 5,770,358, 5,789,162, 5,708,153, 6,040,193 and 5,800,992.

Arrays may be packaged in such a manner as to allow for diagnostic use or can be an all-inclusive device; e.g., U.S. Pat. Nos. 5,856,174 and 5,922,591 incorporated in their entirety by reference for all purposes.

Methods for extension of primers from solid supports have been disclosed for example, in U.S. Pat. Nos. 5,547, 839 and 6,770,751. Methods for genotyping using primer extension have been disclosed, for example, in U.S. Pat. Nos. 5,888,819 and 5,981,176.

An individual is not limited to a human being, but may also include other organisms including but not limited to mammals, plants, bacteria or cells derived from any of the above.

c) Generating Target Sequences Containing One or More Polymorphisms

Generally, the invention provides methods for generating a collection of target sequences containing one or more polymorphisms from a nucleic sample using extension of allele specific probes (capture probes) that are modified to resist proof-reading activity. This allows for the use of a DNA polymerase that has a functional 3' to 5' proof reading activity as described in Lin-Ling et al., Biochem Mol Biol. 38:24-7 (2005), Liao et al., Acta Pharmacol Sin. 26:302-6 (2005), and Zhang et al., Trends Biotechnol. 23:92-96 (2005). The extension may be performed using capture probes that are attached to solid supports, such as beads or glass substrates or capture probes in solution. Modifications that may be used include, for example, phosphorothioate linkages and locked nucleic acid (LNA) modifications that block mismatch excision during proofreading-otherwise the mismatched base would simply be excised and the primer would be extended. Preferably the LNA residue is at the penultimate position of the primer. LNA is further described, for example, in Jepsen et al., Oligonucleotides 14:130-146 (2004) and Petersen and Wengel, Trends Biotechnol 21:746-81 (2003). The methods are related to those disclosed in U.S. Pat. No. 7,108,976, which is incorporated herein by reference in its entirety.

FIG. 1 shows a schematic of allele specific amplification of a selected polymorphic locus. The polymorphism [101] in a double stranded segment of DNA is hybridized with an allele specific primer that is complementary to one strand or the other [103 and 105]. $AS_F$ designates the allele specific forward primer and $AS_R$ the allele specific reverse primer. Similarly, $LS_F$, and $LS_R$ refer to the locus specific forward and reverse primers. In preferred aspects both strands are interrogated, but one of skill in the art will appreciate that either strand may be interrogated individually. The allele specific primer is extended and the extension product is further amplified using the allele specific primer and a locus specific primer [107 and 109] that is complementary to a region downstream of the polymorphism. A separate allele specific primer is designed for each possible allele of the polymorphism. For example, for a biallelic polymorphism there are two allele specific probes, an A and a B allele probe, for each strand being interrogated. If the polymorphism is a SNP with alleles C or T, the allele specific probe to detect the C allele preferably terminates at the 3' end with a G and the allele specific probe to detect the T allele preferably terminates at the 3' end with an A, In preferred aspects the 3' terminal base in the allele specific probe is complementary to the variable position or positions of the polymorphism. In another aspect the penultimate position in the probe is complementary to the variable position.

Figure 2:
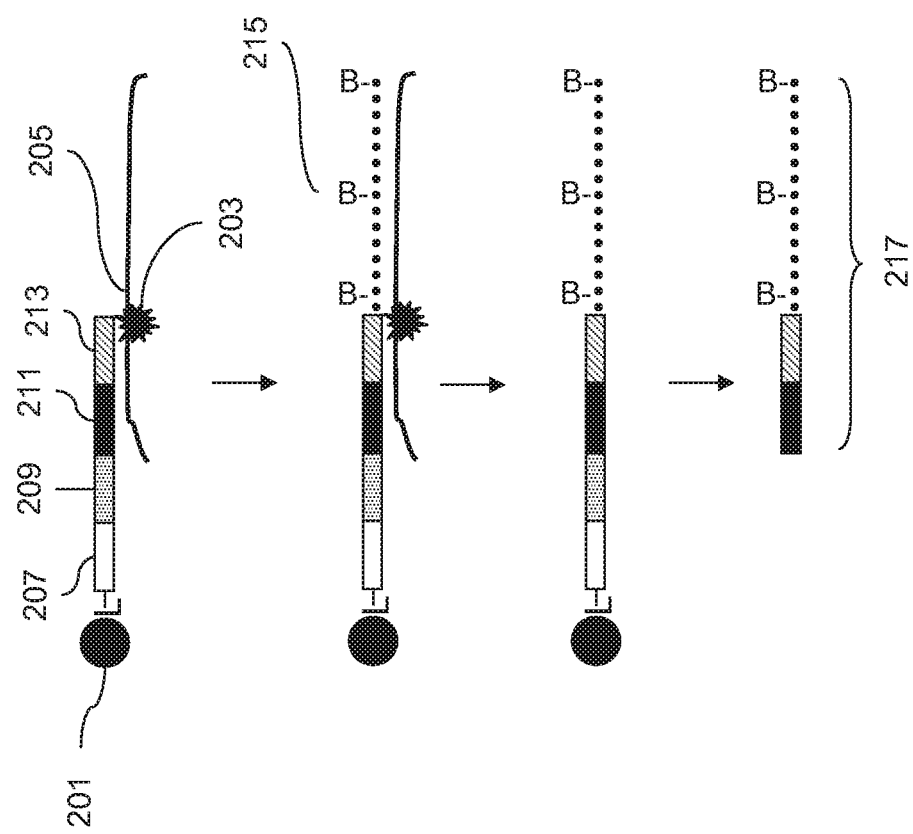
FIG. 2 shows a bead-based allele specific primer extension method.

FIG. 2 shows a method of allele specific primer extension using primers attached to beads [201]. The primer has a poly T region [207], a cleavage region [209], a tag region [211] and an allele specific primer region [213] that is complementary to the target with the 3' base being complementary to the interrogation position [203] in the target [205]. The target hybridizes to the allele specific primer and if there is a perfect match between the 3' end of the primer and the target, the primer is extended using a polymerase with exonuclease activity. Labeled nucleotides are present in the extension reaction and are incorporated into the extension product [215]. Following extension, the extension products may be separated from bound target by denaturation and from other nucleic acid in the sample by separation of the beads from the solution. The target strand may be removed, for example, by washing with 0.15 N NaOH, and the extension product may be cleaved in the cleavage region to release a portion [217] of the extension product that has the tag region, the allele specific region and the labeled extended region. The released product may be detected by hybridization to a tag array. Each different allele to be detected has a different associated tag sequence which hybridizes to a different location on an array of tag probes. In some embodiments the cleavage region [209] includes one or more residues, one or more dI residues, a photo cleavable residue or an enzymatic cleavage site. In another embodiment capture probes and target form hybrids in solution and the hybrids are captured using a bead that has affinity for the capture probe. For example, the capture probe may be labeled at the 5' end with dignoxigenin and captured using a bead coated with anti-digoxigenin or the capture probe may be labeled at the 5' end with biotin and captured with a streptavidin coated bead.

After release from the bead or solid support, the product [217] may then be analyzed by, for example, hybridization to an array as shown in FIG. 3. The figure shows two different extension products [301 and 302] hybridized to different features [311 and 312] of and array. Each feature contains many copies of a different oligonucleotide [307]. The oligonucleotide is complementary to the tag region [303 and 315] of the extended capture probes [301 and 302].

Different features have probes of different sequence so that each feature hybridizes to a different tag sequence. The allele specific primer region of the capture probes [305 and 309] remain single stranded. Information about the region of interest can be determined by analysis of the hybridization pattern. Detection of labeled capture probes at a feature indicates that the allele specific portion of the capture probe attached to a specific tag sequence has been extended so that allele is present in the sample. Additional features [325] are shown. Preferably the array will have more than 1,000, more than 10,000 or more than 100,000 different features each with many copies of a different oligonucleotith, probe sequence complementary to a different tag sequence. For a bialleleic SNP, for example, each allele will have a distinct (allele specific) capture probe that is labeled with a unique tag sequence so that the capture probe for each allele can be separately detected by hybridization to a distinct feature on the array. Individual features may also be beads and features may be present in multiples, for example, 2 or more beads or features with the same probe.

In FIG. 4A the allele specific capture probes [405, 407, 409 and 411] are attached to individual features [413] of an array. The 5' end of the probes is associated with the solid support. In this example allele specific probes are shown for each strand and each allele of the bialleli SNP [401]. Each feature associated with a given SNP interrogates one allele in a strand-specific manner. The discrimination position [415] changes according to the allele to be detected. A single phosphorothioate linkage [403] is shown immediately 5' to the discrimination position.

Figure 4B:
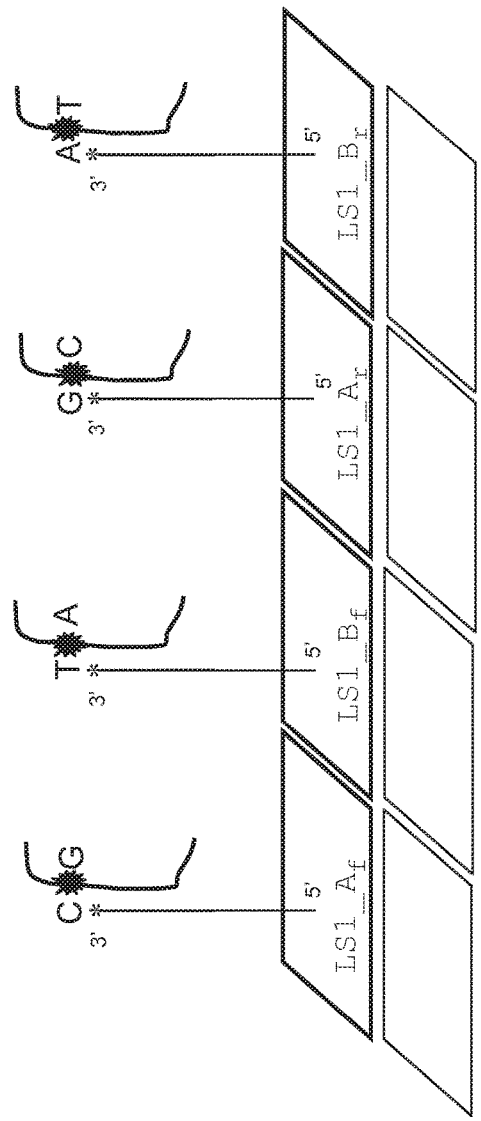
FIG. 4B shows genomic DNA hybridized to the array of allele specific probes with complementarity between the polymorphic base and the 3' end of the probes.
Figure 4C:
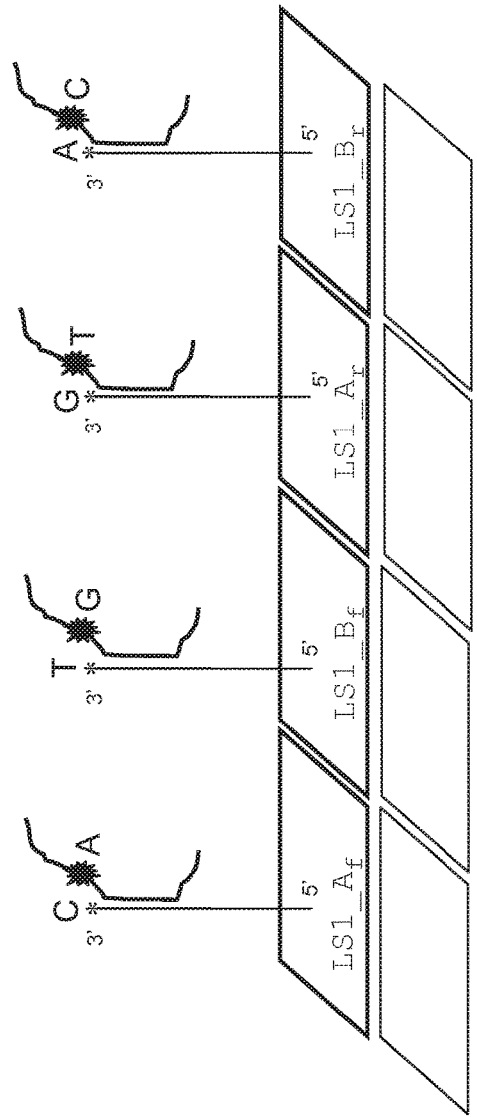
FIG. 4C shows genomic DNA hybridized to the array of allele specific probes with a mismatch between the polymorphic base and the 3' end of the probes.

In FIG. 4B genomic DNA is shown hybridized to the array in a locus specific manner. The capture probes are hybridized with perfectly matched target sequence. In preferred aspect the target is prepared for hybridization by amplifying genomic DNA with an unbiased whole genome amplification method such as Multiple Displacement Amplification or OMNIPLEX amplification. Amplified DNA is fragmented to a size range optimal for hybridization using chemical or enzymatic means prior to hybridization to an array. Increasingly stringent washing conditions are used to remove non-specifically hybridized target and target that has a mismatch at the 3' end of the probe. As shown in FIG. 4C some target may hybridize with a mismatch at the interrogation position, but as shown in FIG. 4D target hybridized with a mismatch should not be extended. FIG. 4D shows extension of the probes that are hybridized in a locus specific manner [441] with incorporation of label (B) and failure to extend and label the probes hybridized with a mismatch at the interrogation position [443]. The mismatch at the terminal base of the capture probe prevents extension of the probe by the DNA polymerase. The extension is performed on the array using a DNA polymerase with 3' to 5' enxonuclease proof reading activity. The primer extension reactions may contain one or more labeled dNTPs, for example a biotinylated nucleotide such as DLR.

The amplified sample may be analyzed by any method known in the art, for example, MALDI-TOF mass spec, capillary electrophoresis, OLA, LCR, RCA, dynamic allele specific hybridization (DASH) or TAQMAN● assays (Applied Biosystems, Foster City, Calif.). For other methods of genotyping analyses see Syvanen, Nature Rev. Gen. 2:930-942 (2001) which is incorporated by reference in its entirety In one embodiment a method for generating a collection of target sequences containing 3' ends specific for each allele for a given SNP using a bead-based solid support is disclosed. (For a description of a bead-based solid support for amplifying complex genomic DNA, see Gunderson et al, Nat. Gen. 37:549-554 (2005) and U.S. Patent Pub. 20050059048, each of which is herein incorporated by reference in its entirety). Each capture probe is attached covalently to a solid support and comprises a spacer sequence, a multiple dU residues, a tag sequence that is unique for each species of capture probe, and a target specific sequence. The solid support is preferably beads but any suitable solid support known in the art may be used, for example, arrays, microparticles, microtitre dishes and gels. In one aspect the bead-based solid support comprises anti-digoxigenin antibodies. The 3'end of the capture probes terminates with a specific nucleotide corresponding to a polymorphism, including the SNP. The 3' end of the capture comprises 0, 1, or 3 phosphorothioate linkages. The spacer sequence may comprise multiple T residues, such as T2 through T12 Preferably, the spacer sequence is a T6. It serves as a linker to move the multiple dU sequences away from the solid support. The multiple dU residues may comprise UIUI or UIUIUI wherein dI represents an inosine base. The multiple dU residues serve as a mechanism to release the oligonucleotides, such as the capture probes, from the solid support. The dU residues can be used with UNG to create an abasic site and then this can lead to back bone cleavage under conditions of high temperature and basic pH. An endonuclease comprising uracil DNA glycosylase (UDG) may be used to cleave the dU residues. Alternatively, dI residues can be used in conjunction with $E.$ $coli$ Endonuclease V to cleave the phosphodiester backbone. Beads with capture probes are loaded and hybridized with fragmented nucleic acid. The fragmented nucleic acid comprises genomic DNA. The beads are then washed and primer extension reaction of the capture probes is carried out using DNA polymerases with exo activity, including exo plus or minus, in combination with capture probes with the phosphorothioate linkage to achieve high allelic specificity. Such DNA polymerases may include mesophilic polymerases, such as T4 DNA polymerase, $E.$ $coli$ Klenow fragment, T7 DNA polymerase, (Taq GOLD™, VENT®, and DEEP VENT®). The DNA polymerase preferably has a 3'→5' exo proofreading activity. There is at least one species of labeled dNTP in each extension reaction. Biotin is one of the labels in one or more species of dNTPs. The labeled nucleotides are incorporated into the extended capture probes. There is one extension reaction wherein four differentially labeled dNTPs are present in the extension reaction. The capture probes are extended on the solid support in a 5' to 3' direction. Nucleic acid fragments, such as genomic DNA, hybridized to the extended capture probes are removed by washing the beads with 0.15 N NaOH. This condition denatures any DNA duplex and results in single stranded DNA. The extended capture probes are then cleaved from the beads either via photo or enzymatic cleavage and hybridized to an array-based solid support comprising a plurality of tag probes. For example, the extended capture probes may contain a photo cleavable biotin modification. Upon exposure to UV light, photo cleavage occurs. The wavelength of the UV light can range from 200 nanometers to 400 nanometers. Enzymatic cleavage includes use of heat or an endonuclease. The tag sequence of the extended capture probes is hybridized to an array comprising a plurality of tag probes. The hybridization pattern is analyzed on each of the arrays to determine at least one genotype. Target sequences containing the polymorphism on the solid support are generated. Each allele-specific capture probe is related to a unique tag array probe.

In another embodiment, a method of generating a collection of target sequences containing a polymorphism, such as a SNP, from a nucleic acid sample on an array-based solid support is disclosed. A collection of capture probes comprises a plurality of different species of primers. A 5' end of the capture probes is bound to an array surface with a spacer sequence and a 3' variable region that is specific for a target sequence in a collection of target sequence. Optionally, the spacer sequence at the 5' end of the capture probes may contain multiple T residues, ranging from two to twelve thymine residues. The 3' end of the capture probes terminate with a specific nucleotide corresponding to a location of SNP. This terminal base is associated with a 0, 1, or 3 phosphorothioate linkage to make the target sequences resistant to proof-reading activity from the DNA polymerases. Each corresponding SNP location interrogates one allele in a strand-specific manner. Nucleic acid sample, such as genomic DNA, is first amplified using a whole genome amplification method, including MDA (using ϕ29 DNA polymerase) or OMNIPLEX amplification (Rubicon Genomics). The amplified genomic DNA is then fragmented to a size range optimal to array hybridization. The fragmented genomic DNA is hybridized to the array containing capture probes. After the hybridization reaction, the array with extended capture probes is washed under a series of increasingly stringent conditions. The wash conditions for the array-based solid support to reduce non-specific hybridization could be from two times of SSC in 0.1% SDS at room temperature to 0.2 times of SSC and 0.1% SDS at an elevated temperature, such as 68° C. Such stringent conditions may prevent target sequences with a mismatch to the 3'end of the capture probes from forming. The hybridization pattern may be analyzed to determine the identity of an allele or alleles present at one or more polymorphic location in the collection of target sequences.

In many embodiments, the nucleic acid samples containing a SNP are amplified in solution without any adapters. The allele-specific forward primers and standard reverse primers for each strand are used to amplify a target specific sequence. The allele-specific forward primers have 0, 1, and 3 phosphorothioate linkages. The DNA. polymerases used have 3' to 5' Exo proof-reading activity. These polymerases may comprise mesophilic polymerases. The DNA polymerases may include Taq GOLD™, VENT®, DEEP VENT®, T4 DNA polymerase, $E$ $coli$ Klenow fragment, or T7 DNA polymerase. The primer extension reaction comprises full or partial substitution of one or more labeled dNTPs. The labeled dNTPs comprise biotin-labelled dNTPs. The array may be substituted for another solid support such as beads, microparticles, microtitre dishes, and gels. The capture probes are extended on a solid support in a 5' to 3' direction. The polymorphism comprises an SNP.

The hybridization and extension of capture probes are done while the capture probes are attached to a solid support. Following extension of the capture probes nucleic acids that are not covalently attached to the solid support may be washed away. The extended capture probes are released from the solid support prior to amplification. Amplification takes place while the extended capture probes are attached to the solid support. The extended capture probes may be released from the solid support by, for example, using a reversible linker or an enzymatic release, such as an endonuclease or by a change in conditions that results in disruption of an interaction between the capture probe and the solid support, for example, when capture probes are associated with the solid support through base pairing between a tag in the capture probe and a tag probe on the solid support, disruption of the base pairing interaction releases the capture probes from the solid support. Enzymatic methods include, for example, use of uracil DNA glycosylase (UDG) or (UNG). UNG catalyzes the hydrolysis of DNA that contains deoxyuridine at the site the uridine is incorporated. Incorporation of one or more uridines in the capture probe followed by treatment with UNG will result in release of the capture probe from the solid support. A thermolabile UNG may also be used Many amplification methods are most efficient amplification of smaller fragments. For example, PCR most efficiently amplifies fragments that are smaller than 2 kb (see, Saiki et al, 1988). The capture probes and fragmentation conditions are selected for efficient amplification of a selected collection of target sequences. The size of the amplified fragments is dependent on where the target specific region of the capture probe hybridizes to the target sequence and the 5' end of the fragment strand that the capture probe is hybridized to. In some embodiments of the present methods capture probes and fragmentation methods are designed so that the target sequence of interest can be amplified as a fragment that is, for example, less than 20,000, 2,000, 800, 500, 400, 200 or 100 base pairs long. The capture probe can be designed so that the 3' end of the target specific region hybridizes to the base that is just 3' of a position to be interrogated in the target sequence. For example, if the sequence to be interrogated is a polymorphism and the sequence is 5'-GCTXATCGG-3', where X is the polymorphic position, the target specific region of the capture probe may have the sequence 5'---CCGAT-3'. When the sample is fragmented with site specific restriction enzymes the length of the fragments will also depend on the position of the nearest recognition site for the enzyme or enzymes used for fragmentation. A collection of target sequences may be selected based on proximity to restriction sites. The target sequences are selected for amplification and analysis based on the presence of a sequence of interest, such as a SNP, and proximity to a cleavage site for a selected restriction enzyme. For example, SNPs that are within 200, 500, 800, 1,000, 1,500, 2,000 or 20,000 base pairs of either a restriction site, such as, for example, an EcoRI site, a BglI site, an XbaI site or any other restriction enzyme site may be selected to be target sequences in a collection of target sequences. In another method a fragmentation method that randomly cleaves the sample into fragments that are 30, 100, 200, 500 or 1,000 to 100, 200, 500, 1,000 or 2,500 base pairs on average may be used.

To detect the allele or alleles present the amplified fragments are digested with a Type IIs restriction endonuclease and the fragments are extended in the presence of labeled ddNTPs. The fragments will be extended by a single ddNTP which corresponds to the allele present at the polymorphic position. The extended fragments are hybridized to an array of tag probes and the labeled nucleotide or nucleotides present at each location are determined. The ddNTPs are all labeled with the same label, for example, biotin and the fragments are extended in four separate reactions, one for each of the four different ddNTPs. Each reaction is hybridized to a different array so four arrays are used. In another embodiment the ddNTPs are labeled with differentially detectable labels. There are four different labels and the extension reaction may be done in a single reaction and the hybridization may be to a single array. There can be two different labels and extension reaction may be done in two reactions and the hybridization may be to two different arrays.

In the present methods one or more enrichment step may be included to generate a sample that is enriched for extended capture probes prior to amplification with common sequence primers. It is desirable to separate extended capture probes from fragments from the starting nucleic acid sample, adapter-ligated fragments, adapter sequences or non-extended capture probes, for example. In one embodiment the capture probes are extended in the presence of a labeled dNTP, for example dNTPs labeled with biotin. The labeled nucleotides are incorporated into the extended capture probes and the labeled extended capture probes are then separated from non-extended material by affinity chromatography. When the label is biotin the labeled extended capture probes can be isolated based on the affinity of biotin for avidin, streptavidin or a monoclonal anti-biotin antibody. In one embodiment the antibody may be coupled to protein-A agarose, protein-A SEPHAROSE® or any other suitable solid support known in the art. Those of skill in the art will appreciate that biotin is one label that may be used but any other suitable label or a combination of labels may also be used, such as fluorescein which may be incorporated in the extended capture probe and an anti-fluorescein antibody may be used for affinity purification of extended capture probes. Other labels such as, digoxigenin, Cyanine-3, Cyanine-5, Rhodarnine, and TEXAS RED® (i.e., sulforhodamine 101 acid chloride) may also be used. Antibodies to these labeling compounds may be used for affinity purification. Also, other haptens conjugated to dNTPs may be used, such as, for example, dinitrophenol (DNP).

The extension products may be enriched by circularization followed by digestion with a nuclease such as Exonuclease VII or Exonuclease III. The extended capture probes may be circularized, for example, by hybridizing the ends of the extended capture probe to an oligonucleotide splint so that the ends are juxtaposed and ligating the ends together. The splint will hybridize to the A1 and A2 sequences in the extended capture probe and bring the 5' end of the capture probe next to the 3' end of the capture probe so that the ends may be ligated by a ligase, for example DNA Ligase or AMPLIGASE® Thermostable DNA. See, for example, U.S. Pat. No. 5,871,921 which is incorporated herein by reference. The circularized product will be resistant to nucleases that require either a free 5' or 3' end.

A variety of nucleases may be used in one or more of the embodiments. Nucleases that are commercially available and may be useful in the present methods include: Mung Bean Nuclease, E. Coli Exonuclease I, Exonuclease III, Exonuclease VII, T7 Exonuclease, BAL-31 Exonuclease, Lambda Exonuclease, RecJ$_f$, and Exonuclease T. Different nucleases have specificities for different types of nucleic acids making them useful for different applications. Exonuclease I catalyzes the removal of nucleotides from single-stranded DNA in the 3' to 5' direction. Exonuclease I degrades excess single-stranded primer oligonucleotide from a reaction mixture containing double-stranded extension products. Exonuclease III catalyzes the stepwise removal of mononucleotides from 3'-hydroxyl termini of duplex DNA. A limited number of nucleotides are removed during each binding event, resulting in coordinated progressive deletions within the population of DNA molecules. The preferred substrates are blunt or recessed 3'-termini, although the enzyme also acts at nicks in duplex DNA to produce single-strand gaps. The enzyme is not active on single-stranded DNA, and thus 3'-protruding termini are resistant to cleavage. The degree of resistance depends on the length of the extension, with extensions 4 bases or longer being essentially resistant to cleavage. This property can be exploited to produce unidirectional deletions from a linear molecule with one resistant (3'-overhang) and one susceptible (blunt or 5'-overhang) terminus, Exonuclease VII is a single-strand directed enzyme with 5' to 3'- and 3' to 5'-exonuclease activities making it the only bi-directional *E. coli* exonuclease with single-strand specificity. The enzyme has no apparent requirement for divalent cation, and is fully active in the presence of EDTA. Initial reaction products are acid-insoluble oligonucleotides which are further hydrolyzed into acid-soluble form. The products of limit digests are small oligomers (dimers to dodecamers). For additional information about nucleases see catalogs from manufacturers such as New England Biolabs, Beverly, Mass.

In some embodiments one of the primers added for PCR amplification is modified so that it is resistant to nuclease digestion, for example, by the inclusion of phosphorothioate. Prior to hybridization to an array one strand of the double stranded fragments may be digested by a 5' to 3' exonuclease such as T7 Gene 6 Exonuclease.

In some embodiments the nucleic acid sample, which may be, for example, genomic DNA, is fragmented, using for example, a restriction enzyme, DNase I or a non-specific fragmentation method such as that disclosed in U.S. Pat. No. 6,495,320, which is incorporated herein by reference in its entirety. Adapters containing at least one priming site are ligated to the fragmented DNA. Locus-specific primers are synthesized which contain a different adapter sequence at the 5' end. The adapter-ligated genomic DNA is hybridized to the locus-specific primers and the locus specific primer is extended. This may be done for example, by the addition of DNA polymerase and dNTPs. Extension products may be amplified with primers that are specific for the adapter sequences. This allows amplification of a collection of many different sequences using a limited set of primers. For example, a single set of primers maybe used for amplification. In another embodiment a second amplification step is carried out using the same or different primers.

In some embodiments a collection of target sequences is analyzed. A plurality of capture probes is designed for a plurality of target sequences. In some embodiments target sequences contain or are predicted to contain a polymorphism, for example, a SNP. The polymorphism may be, for example, near a gene that is a candidate marker for a phenotype, useful for diagnosis or a disorder or for carrier screening or the polymorphism may define a haplotype block (see, Daly et al. *Nat, Genet,* 29:229-32 (2001), and Rioux et al. *Nat. Genet,* 29:223-8 (2001) and U.S. Patent Publication Number 20030170665 each of which is incorporated herein by reference in its entirety). A collection of capture probes may be designed so that capture probes hybridize near a polymorphism, for example, within 1, 5, 10, or 100 to 5, 10, 100, 1000, 10,000 or 100,000 bases from the polymorphism. The capture probes hybridize to one strand of the target sequence and can be extended through the polymorphic site or region so that the extension product comprises a copy of the polymorphic region.

The amplified products are analyzed by hybridization to an array of probes attached to a solid support. In some embodiments an array of probes is specifically designed to interrogate a collection of target sequences. The array of probes may interrogate, for example, from 1,000, 5,000, 10,000 or 100,000 to 2,000, 5,000, 10,000, 100,000, 1,000, 000 or 3,000,000 different target sequences. In one embodiment the target sequences contain SNPs and the array of probes is designed to interrogate the allele or alleles present at one or more polymorphic location. The array may comprise a collection of probes that hybridize specifically to one or more SNP containing sequences. The array may comprise probes that correspond to different alleles of the SNP. One probe or probe set may hybridize specifically to a first allele of a SNP, but not hybridize significantly to other alleles of the SNP and a second probe set may be designed to hybridize to a second allele of a SNP but not hybridize significantly to other alleles. A hybridization pattern from the array indicates which of the alleles are present in the sample. An array may contain probe sets to interrogate, for example, from 1,000, 5,000, 10,000 or 100,000 to 2,000, 5,000, 10,000, 100,000, 1,000,000 or 3,000,000 different SNPs.

An array of probes that are complementary to tag sequences present in the capture probes is used to interrogate the target sequences. In some embodiments the amplified targets are analyzed on an array of tag sequences, for example, the Affymetrix GenFlex● array or Universal Tag Array (3K, 5K, 10K or 25K) (Affymetrix, Inc., Santa Clara, Calif.). In this embodiment the capture probes comprise a tag sequence that is unique for each species of capture probe. A detectable label that is indicative of the allele present at the polymorphic site of interest is associated with the tag. The labeled tags are hybridized to the one or more arrays and the hybridization pattern is analyzed to determine which alleles are present.

EXAMPLES

Example 1

Msp Digestions of HTR2A PCR Product

HTR2A PCR products were taken from 16 individuals, digested with the restriction enzyme Msp and the samples were run on a gel. The genotypes of the 16 individuals were the following: 1 individual with a TT genotype, 7 individuals with a CT genotype, and 8 individuals with a CC genotype. Individuals with a CT genotype produce two distinct bands on the gel in which the second band is aligned equally with one band produced for individuals with CC genotype. The first band of the CT genotype is higher on the gel than CC genotype band. Individuals with TT genotype have one distinct band that is higher on the gel than the individuals with CC genotype. The experiment shoved that Msp digestion worked on individuals with a CT genotype.

Example 2

Exonuclease Sensitivity of Primers

Allele specific forward primers were run with different polymerases and phosphorothioate linkages. The primers were incubated with no enzyme, VENT® polymerase, DEEP VENT® polymerase, and DEEP VENT® (exo-) polymerase with 0, 1 and 3 phosphorothioate linkages. All products were incubated at 72° C. for 45 minutes. The products were run on a 8M urea 15% acrylamide gel and stained with SYBR® Green. No distinct bands were observed in the lanes where the primers had 0 phosphorothioate linkages in the VENT® polymerase or DEEP VENT® polymerase lanes. Distinct bands were found in other lanes. The experiment showed that allele specific forward primers are resistant to 3'to 5' exonuclease activity only if they contain at least one phosphorothioate linkage.

Example 3

Phosphorothioate Linkages Increase Specificity of PCR

Samples were run on a gel with individuals with CC genotype, TT genotype, and no DNA and these samples varied with 0, 1, and 3 phosphorothioate linkages. The gels were on Pfu Ultra at 55° C., 60° C., and 65° C. The results showed that no bands in the no DNA lanes at all temperatures. Bands were visible in lanes with 1 or 3 phosphorothioate linkages with respect to CC genotype and TT genotype at all temperatures. However, no band was visible in the TT genotype lane with 0 phosphorothioate linkages at all temperatures. The results indicate phosphorothioate linkages help to increase the specificity of standard solution phase PCR.

Example 4

Cleavage from Solid Support

Two long allele-specific oligonucleotides necessary for the bead based approach were treated and run on a gel. The products were treated with no treatment, Streptavidin, UV light, Streptavidin+UV light, *E. Coli* Endo V, and Endo V+Streptavidin. The products were run on a 6%, 8M urea acrylamide gel and stained with SYBR® Green. This gel uses SA gel shift after various types of treatments to show the modular nature of the oligos. The results showed that two bands were observed in the UV light+streptavidin and Endo V+Streptavidin lanes. The two bands indicated that photocleavage (UV light) and enzymatic cleavage (Endo V) worked in the presence of streptavidin on those particular DNA strands. Multiple bands were observed in the streptavidin lanes while single distinct bands were observed in all other lanes.

CONCLUSION

From the foregoing can be seen that the present invention provides a flexible and scalable method for analyzing complex samples of DNA, such as genomic DNA. These methods are not limited to any particular type of nucleic acid sample: plant, bacterial, animal (including human) total genome DNA, RNA, cDNA and the like may be analyzed using some or all of the methods disclosed in this invention. This invention provides a powerful tool for analysis of complex nucleic acid samples. From experiment design to isolation of desired fragments and hybridization to an appropriate array, the above invention provides for fast, efficient and inexpensive methods of complex nucleic acid analysis.

All patents, publications and patent applications cited above are incorporated by reference in their entirety for all purposes to the same extent as if each individual patent, publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

The invention claimed is:

1. A method of genotyping one or more polymorphisms in a nucleic acid sample comprising:
    amplifying the nucleic acid sample via polymerase chain reaction;
    mixing the amplified nucleic acid sample with one or more pairs of capture probes to form a capture probe mixture, wherein each pair of capture probes includes a first allele-specific primer having a first allele-specific region that is complementary to a first allele of a selected polymorphism and includes the polymorphic position, and
    a second allele-specific primer having a second allele-specific region that is complementary to a second allele of the selected polymorphism and includes the polymorphic position,
    wherein the first and second allele-specific primers omit common primer sequences 5' of their respective allele-specific regions, and
    wherein the 5' end of each capture probe is connected to an initial solid support;
    subjecting the capture probe mixture to a primer extension reaction, wherein said first and second allele-specific primers are extended with a DNA polymerase to generate first and second allele-specific extension products in the presence of the first and second alleles, respectively;
    cleaving the first and second allele-specific extension products from the initial solid support, and hybridizing said first and second allele-specific extension products with a subsequent solid support; and
    detecting the presence of said first and second allele-specific extension products, wherein the presence of a first allele-specific extension product is indicative of the presence of the first allele of a selected polymorphism and the presence of a second allele-specific extension product is indicative of the presence of the second allele,
    wherein the first allele-specific primer comprises a first tag region, which is included in the first allele-specific extension product and the second allele-specific primer comprises a second tag region, which is included in the second allele-specific extension product.

2. The method of claim 1, wherein the nucleic acid sample amplified in the step of amplifying the nucleic acid sample via polymerase chain reaction is a genomic DNA sample.

3. The method of claim 1, wherein the method further comprises fragmenting the nucleic acid sample to generate fragments prior to or after the step of amplifying the nucleic acid sample via polymerase chain reaction.

4. The method of claim 1, wherein in said primer extension reaction there is at least one species of labeled ddNTP.

5. The method of claim 1, wherein the subsequent solid support is selected from the group consisting of arrays, beads, microparticles, microtiter dishes and gels.

6. The method of claim 1, wherein said first and second allele-specific extension products are associated with the subsequent solid support through hybridization between the tag regions and corresponding tag probes on the subsequent solid support.

7. The method of claim 1, wherein said DNA polymerase comprises a proofreading activity.

8. The method of claim 1, wherein the first and second allele-specific extension products are not amplified between being formed and prior to being detected.

9. The method of claim 1, wherein the first and second allele-specific extension products are not amplified between being cleaved from the initial solid support and prior to being detected.

10. The method of claim 1, wherein the first tag region is immediately adjacent the first allele-specific region, and the second tag is region immediately adjacent the second allele-specific region.

11. A method for genotyping one or more polymorphisms in a nucleic acid sample, where each polymorphism has a first and a second allele, comprising:
    amplifying the nucleic acid sample via polymerase chain reaction;

incubating the amplified nucleic acid sample with one or more allele-specific capture probes to allow formation of complexes between target sequences and allele-specific capture probes, wherein the allele-specific capture probes comprise
- a target-specific region that terminates at its 3' end with a base that is complementary to a polymorphic base in the target sequence,
- a tag region immediately adjacent the target-specific region, wherein each different allele-specific probe has a different sequence tag region, and
- wherein the 5' ends of the allele-specific capture probes are connected to an initial solid support;

extending the allele-specific capture probes in the presence of labeled nucleotides using the target sequence as a template to obtain labeled allele-specific capture probes, wherein extension of the allele-specific capture probes is blocked if there is a mismatch between the polymorphic position and the 3' end of the allele-specific capture probe;

cleaving the labeled allele-specific capture probes from the initial solid support, and hybridizing the labeled allele-specific capture probes with a subsequent solid support; and determining the genotype of said polymorphisms by determining which alleles are present, wherein the presence of labeled allele-specific capture probes is indicative of the presence of a particular allele in the nucleic acid sample.

12. The method of claim 11, wherein the nucleic acid sample amplified in the step of amplifying the nucleic acid sample via polymerase chain reaction is a genomic DNA sample.

13. The method of claim 11, wherein the method further comprises fragmenting the nucleic acid sample to generate fragments prior to or after the step of amplifying the nucleic acid sample via polymerase chain reaction.

14. The method of claim 11, wherein the method further comprises separating the target sequence from the labeled allele-specific capture probes.

15. The method of claim 11, wherein the subsequent solid support is selected from the group consisting of arrays, beads, microparticles, microtiter dishes and gels.

16. The method of claim 11, wherein the labeled allele-specific capture probes are associated with the subsequent solid support through hybridization between the tag region and a tag probe on the subsequent solid support that is complementary to the tag region.

17. The method of claim 11, wherein said allele-specific capture probes are extended in the presence of a DNA polymerase which comprises a proofreading activity.

18. A method of genotyping one or more polymorphisms in a nucleic acid sample comprising:

amplifying the nucleic acid sample via polymerase chain reaction;

mixing the amplified nucleic acid sample with one or more pairs of capture probes to form a mixture, wherein each pair of capture probes includes
- a first allele-specific primer having a first allele-specific region that is complementary to a first allele of a selected polymorphism and includes the polymorphic position, with a first tag region immediately 5' of the first allele-specific region, and
- a second allele-specific primer having a second allele-specific region that is complementary to a second allele of the selected polymorphism and includes the polymorphic position, with a second tag region immediately 5' of the second allele-specific region,
- wherein the first and second allele-specific primers omit common primer sequences 5' of their respective allele-specific regions, and
- wherein the 5' end of each capture probe is connected to an initial solid support;

subjecting the mixture to a primer extension reaction, wherein said first and second allele-specific primers are extended with a DNA polymerase to generate first and second allele-specific extension products in the presence of the first and second alleles, respectively;

cleaving the first and second allele-specific extension products from the initial solid support and hybridizing said first and second allele-specific extension products with a subsequent solid support, wherein the subsequent solid support is selected from the group consisting of arrays, beads, microparticles, microtiter dishes and gels; and detecting the presence of said first and second allele-specific extension products, wherein the presence of a first allele-specific extension product is indicative of the presence of the first allele of a selected polymorphism and the presence of a second allele-specific extension product is indicative of the presence of the second allele, wherein the first allele-specific primer comprises a first tag region, which is included in the first allele-specific extension product and the second allele-specific primer comprises a second tag region, which is included in the second allele-specific extension product, and wherein said first and second allele-specific extension products are associated with the subsequent solid support through hybridization between the tag regions and corresponding tag probes on the subsequent solid support.

* * * * *